United States Patent [19]

Cremascoli

[11] Patent Number: 4,813,959

[45] Date of Patent: Mar. 21, 1989

[54] HIP PROTHESIS STRUCTURE COMPRISING A FEMORAL COMPONENT AND AN ACETABULAR COMPONENT

[76] Inventor: Patrizio Cremascoli, Via Clemente Prudenzio, 14/16 -- 20138 Milano, Italy

[21] Appl. No.: 134,947

[22] Filed: Dec. 18, 1987

[30] Foreign Application Priority Data

Jan. 28, 1987 [IT] Italy ................ 19187 A/87

[51] Int. Cl.⁴ ............................ A61F 2/32; A61F 2/30
[52] U.S. Cl. ........................................ 623/22; 623/23; 623/18
[58] Field of Search ........................ 623/16, 18, 22, 23

[56] References Cited

U.S. PATENT DOCUMENTS 4,566,138  1/1986  Lewis et al. ............................ 623/22
4,599,085  7/1986  Riess et al. ............................. 623/18

FOREIGN PATENT DOCUMENTS 0065482  11/1982  European Pat. Off. ............. 623/22
1446097  8/1976  United Kingdom .................. 623/18

Primary Examiner—Richard J. Apley
Assistant Examiner—David J. Isabella
Attorney, Agent, or Firm—Bucknam and Archer

[57] ABSTRACT

A total hip prosthesis structure comprises an acetabolar or socket component (1) and a femoral or pin component (2), these components being made of a metal or metal alloy and being intimately connected to parts of ceramic material at least part of the surface of which (other than that in contact with the metal part) is granular or porous so as to encourage osteogenesis after implantation. The metal part (3) of the acetabular component (1) is shaped in such a way as to simplify and facilitate its anchorage in the corresponding cavity of the ilium by having a sharp screw thread (4) thereon.

1 Claim, 2 Drawing Sheets

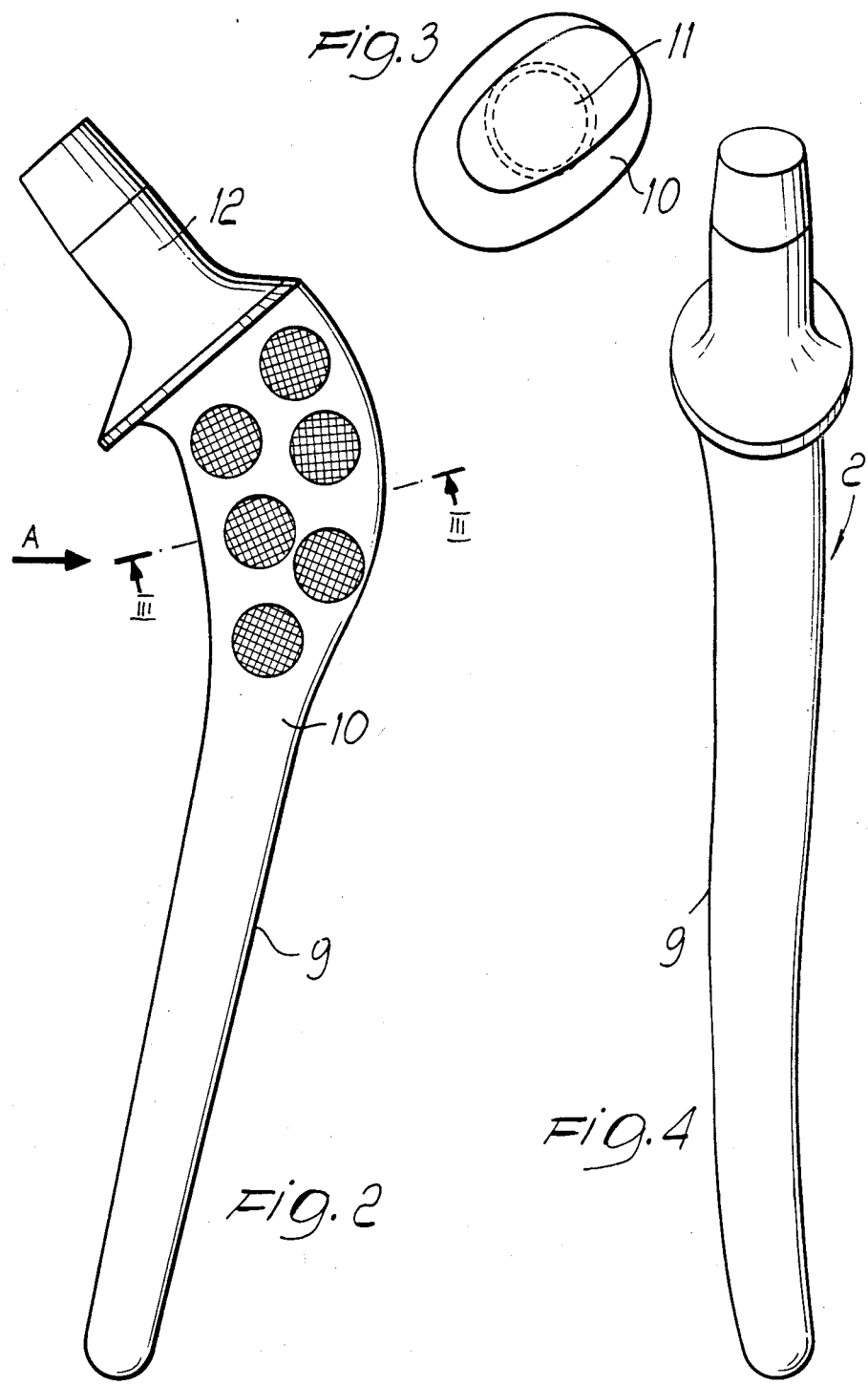

HIP PROTHESIS STRUCTURE COMPRISING A FEMORAL COMPONENT AND AN ACETABULAR COMPONENT

The present invention relates to a hip prosthesis structure, comprising a femoral component and an acetabular component, both made partly of metal and partly of ceramic.

Hip prostheses as such are known, these being of various different types: for correcting loss of articulation of the femur it is known to use a so-called "total" hip prosthesis having a component to replace the head of the femur and a componment to replace the acetabulum in which the head of the femur is housed. Currently, such prostheses are made either of porous metal or ceramic although in both cases there are practical disadvantages both as far as the initial fitting of the prosthesis is concerned and subsequent stabilisation in place.

The object of the present invention is to overcome the disadvantages of known metal and ceramic prostheses by providing a total hip prosthesis structure which includes a socket directly screwable into the iliac bone.

According to the present invention there is provided a total hip prosthesis structure comprising an acetabulum or socket component and a femoral or pin component, characterized in that both said components have a body portion made of a metal alloy to which are intimately connected parts of ceramic material which is granular or porous at least at the surface thereof, the metal body portion of the acetabulum component thereof being shaped so as to simplify and facilitate anchorage in the corresponding cavity of the ilium.

An important advantage of the present invention is that it provides a total hip prosthesis structure in which the biological stabilisation of its component parts within the bone after implanting is greatly facilitated.

Another advantage of the present invention is that it provides a total hip prosthesis structure in which the coupling prosthetic acetabulum and the head of the femur has a very low coefficient of friction.

One embodiment of the present invention will now be more particularly described, by way of example, with reference to the accompanying drawings, in which:

FIG. 2 is a longitudinal section of a femoral pin component of the total hip prosthesis structure of the invention;

FIG. 3 is a transverse section of the femoral pin component of FIG. 2, taken on the line III—III of FIG. 2; and FIG. 4 is a view of the femoral pin of FIGS. 2 and 3 seen from the direction of the arrow A of FIG. 2.

Figure 1:
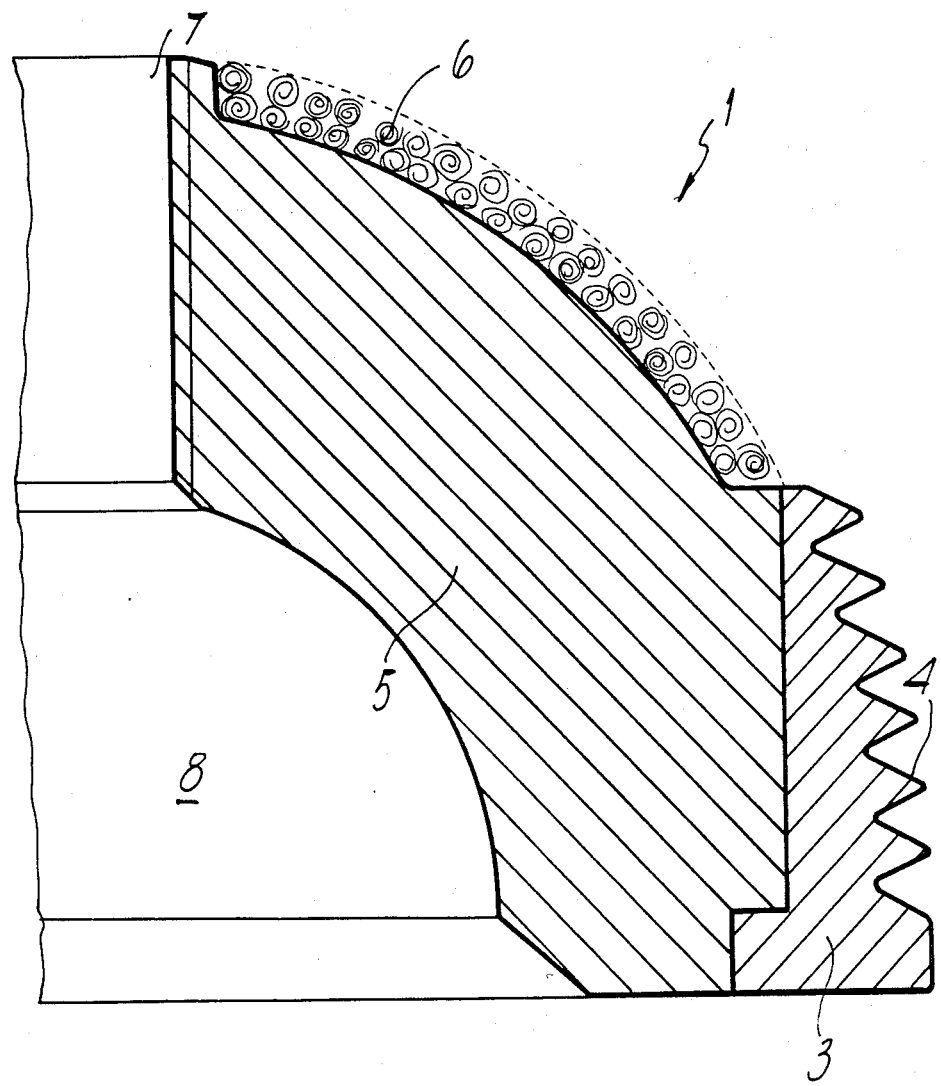
FIG. 1 is a partial section of the acetabulum component of a total hip prosthesis structure constituting an embodiment of the invention.

Referring now to the drawings the total hip prosthesis structure shown comprises an acetabulum or socket component generally indicated with the reference numeral 1, and a femoral or pin component generally indicated 2. The acetabulum component is constituted by a metal annular body 3 made, for example, of titanium alloy, provided with an external circumferential thread 4. This annular body 3 houses within its interior a hollow ceramic insert 5 made, for example, of alumina and shaped in such a way as to present a characteristic hemispherical form.

The said ceramic component is fitted into the metal element preferably by hot or cold casting, and is held securely in place by the high pressure which develops between the outer ceramic surfaces and inner metal surfaces after cooling of the metal. The part of the surface of the ceramic insert not intended to be coupled to the metal is then covered with a single, double, or plural layer of crushed granular material 6.

This layer is also composed of ceramic material for the purpose of permitting an adequate re-growth of bone between its superficial interstices for socket-bone anchorage. Bone re-growth eventually fills the narrow spaces created by the superimposed layers of ceramic granules, this layer can consequently be considered to act as a porous material. The term "ceramic granules" is intended to mean both ceramic grains of spherical or other form, even irregular, the individual dimensions of which can vary between 0.100 and 2.000 millimeters.

The said ceramic insert 5 has an axial through-hole 7 and a part-spherical cavity 8 which can receive the part-spherical head (not shown) of the femur on the head end 12 of the femoral pin generally indicated 9, and having an elongate form enabling it to be inserted into a suitably prepared medullary canal in the femur.

This femoral pin is composed, in turn, of a metal base element 10 for example of titanium alloy, let into the surface of which are a plurality of granulated ceramic inserts 11 in single or plural layers, for the purpose of encouraging the anchorage of the pin to the surrounding bone. These ceramic inserts, which in FIG. 2 have a circular form, can obviously be of any form and dimensions whatsoever according to the specific constructional and/or functional requirements.

In particular, the said metal parts can be made in titanium, titanium alloys, stainless steel, chrome-cobalt alloys and the like, whilst the ceramic parts can be made with alumina, calcium aluminate, procelain, bio-glass, zirconium oxides, titanium oxides, apatites of any type, hydroxyapatites, sialon ceramics and the like, or even any combination thereof.

In substance, the prosthesis structure thus formed permits the following advantages to be obtained. First, improved osteogenesis (bone growth) within an environment—the ceramic—the bio-capatibility of which is much greater than that of a similar "porous" metal implant because of the greater chemical stability of the ceramic components with respect to those of metal alloys; second, the possibility of screwing the acetabulum member to the bone without the necessity of a preliminary tapping, thanks to the fact that the threads of the metal ring can be made sharp, which is not technically possible in an entirely ceramic socket. A further advantage of the prosthesis of the present invention is the total absence of parts made of polyethylene or other plastics material which can be the cause of micro-detritus which is not tolerated by the organism. Finally, the use of ceramic for the acetabulum component allows the possibility of highly polishing the surface so as to make possible a coupling with low co-efficient of friction between the prosthetic acetabulum socket and the head of the femur.

I claim:

1. A total hip prosthesis comprising an acetuabulum component (1) and a femoral component (2), both said components having a body portion made of a metal alloy to which are intimately connected parts of ceramic material which is porous at least at an exposed surface thereof said ceramic material includes ceramic porous inserts which are fitted to said metal body by casting; and, the acetabulum component consisting of an annular ring-like metal shell having an external circumferential threaded portion for engaging the bony tissues and an interior surface shaped to receive a ceramic cup, said cup having an inner part-spherical concavity, to engage a spherical head of the femoral component, and an outer dome shaped surface wherein said ceramic cup is fixedly secured to said interior surface of the annular ring-like metal shell resulting in an exposed polar region of said dome shaped surface said exposed polar region having at least one porous coating thereon; and said ceramic cup having an axial through-hole in the polar region thereof.

* * * * *